United States Patent
Droit et al.

(10) Patent No.: US 10,702,189 B2
(45) Date of Patent: Jul. 7, 2020

(54) SENSOR MEASURING PATIENT SPINE VERTEBRA ANGULAR ORIENTATION

(71) Applicant: ONEFIT MEDICAL, Besancon (FR)

(72) Inventors: Christophe Droit, Montarlot-les-Rioz (FR); Joe Hobeika, Besancon (FR); Rëmi Hugonnet, Roulans (FR); Sébastien Henry, Baume les Dames (FR)

(73) Assignee: EOS IMAGING, Paris (FR)

(*) Notice: Subject to any disclaimer, the term of this patent is extended or adjusted under 35 U.S.C. 154(b) by 275 days.

(21) Appl. No.: 15/774,153

(22) PCT Filed: Nov. 6, 2015

(86) PCT No.: PCT/IB2015/002244
§ 371 (c)(1),
(2) Date: May 7, 2018

(87) PCT Pub. No.: WO2017/077356
PCT Pub. Date: May 11, 2017

(65) Prior Publication Data
US 2018/0325423 A1    Nov. 15, 2018

(51) Int. Cl.
*A61B 5/107*   (2006.01)
*A61B 5/00*    (2006.01)
(Continued)

(52) U.S. Cl.
CPC ........... *A61B 5/1071* (2013.01); *A61B 5/103* (2013.01); *A61B 5/4561* (2013.01);
(Continued)

(58) Field of Classification Search
CPC . A61B 17/7074; A61B 34/10; A61B 17/7011; A61B 17/7013; A61B 17/7079; A61B 17/708; A61B 17/8863
(Continued)

(56) References Cited

U.S. PATENT DOCUMENTS 5,772,610 A * 6/1998 McGorry ............. A61B 5/1071
                                                    33/512
9,585,700 B2    3/2017 Wehrle et al.
(Continued)

FOREIGN PATENT DOCUMENTS

EP    2 910 206    8/2015
KR    101 438 714    9/2014
WO    WO 94/07414    4/1994

OTHER PUBLICATIONS

International Search Report, PCT/IB2015/002244, dated Oct. 5, 2016.
A. Tafallol et al: "Lumbopelvic rhythm during forward and backward sagittal trunk rotations: Combined in vivo measurement with inertial tracking device and biomechanical modeling", Clinical Biomechanics., vol. 29, No. 1, Jan. 1, 2014 (Jan. 1, 2014), pp. 7-13, XP055292241, GB ISSN: 0268-0033, D01: 10.1016/j.clinbiomech. 2013.10.021.

*Primary Examiner* — Yaritza Guadalupe-McCall
(74) *Attorney, Agent, or Firm* — Young & Thompson

(57) ABSTRACT

Disclosed is a sensor measuring patient spine vertebra angular orientation, including: a fastener, adapted to be fastened on a specific patient spine vertebra in a unique orientation relative to the specific vertebra, a support, solidary with the fastener in a unique orientation relative to the fastener, a detector, removably secured to the support in a unique orientation relative to the support and adapted to measure one or more parameters representative of the patient spine vertebra angular orientation.

22 Claims, 2 Drawing Sheets

(51) Int. Cl.
  *A61F 2/46* (2006.01)
  *A61B 17/70* (2006.01)
  *A61B 5/103* (2006.01)
  *A61F 2/44* (2006.01)
  *A61B 34/20* (2016.01)

(52) U.S. Cl.
  CPC .......... *A61B 5/4566* (2013.01); *A61B 5/6878* (2013.01); *A61B 17/7074* (2013.01); *A61F 2/4657* (2013.01); *A61B 5/002* (2013.01); *A61B 5/6884* (2013.01); *A61B 2034/2048* (2016.02); *A61B 2505/05* (2013.01); *A61B 2562/0219* (2013.01); *A61B 2562/04* (2013.01); *A61F 2/44* (2013.01); *A61F 2002/4668* (2013.01)

(58) Field of Classification Search
  USPC .......................................................... 33/512
  See application file for complete search history.

(56) References Cited

U.S. PATENT DOCUMENTS

| | | | |
|---|---|---|---|
| 2005/0096535 A1 | 5/2005 | de la Barrera | |
| 2007/0149899 A1* | 6/2007 | Shechtman | A61B 5/103 600/587 |
| 2016/0106477 A1* | 4/2016 | Hynes | A61B 17/7044 606/279 |
| 2016/0106479 A1* | 4/2016 | Hynes | A61B 17/7059 606/286 |
| 2018/0125598 A1* | 5/2018 | McAfee | A61F 2/4657 |
| 2018/0325423 A1* | 11/2018 | Droit | A61B 5/6878 |

\* cited by examiner

SENSOR MEASURING PATIENT SPINE VERTEBRA ANGULAR ORIENTATION

FIELD OF THE INVENTION

The invention relates to sensors measuring patient spine vertebra angular orientation, to sets of sensors measuring patient spine vertebra angular orientation, and to methods using a set of sensors measuring patient spine vertebra angular orientation.

BACKGROUND OF THE INVENTION

According to a prior art, for example disclosed in patent application U.S. 2005 0096535, it is known a peroperative planning method for recording image of digital markers to get position and orientation of a knee joint.

A first drawback of this prior art method is the need to access some articulation surfaces which would be more difficult to access in a vertebral column than it was in a knee joint.

A second drawback of this prior art method is the intrinsically relatively complex implementation of those digital markers, which are to be positioned at different places on the articulation or in its immediate vicinity. This complexity is all the more detrimental that the articulation becomes complex or presents key vertebrae surfaces more difficult to access. This would especially be the case, if it was to be implemented on the vertebrae of a spine.

SUMMARY OF THE INVENTION

The object of the present invention is to alleviate at least partly the above mentioned drawbacks.

More particularly, the invention aims to provide for a sensor and also a set of sensors which allows for a precise vertebra angular orientation measurement while being relatively simple and cheap.

Embodiments of the invention provide for a sensor, and also a set of sensors, which will on the one side be sufficiently specific to allow for precise vertebra angular orientation measurement fully adapted to a specific patient and on the other side be sufficiently generic to allow for simple sensor structure and for relatively cheap overall cost of the set of sensors needed to perform the required measurement.

Embodiments of the invention provide for a sensor which presents simultaneously a specific fastener for each vertebra of the patient, to improve measurement precision, as well as a detector removably secured to its support, in order to lower overall cost of the required set of sensors.

Embodiments of the invention allow for measuring this spine vertebra angular orientation, based on a patient spine image reconstructed only from two 2D x-ray images, a frontal one and a lateral one.

This object is achieved with a sensor measuring patient spine vertebra angular orientation, comprising: a fastener, adapted to be fastened on a specific patient spine vertebra in a unique orientation relative to said specific vertebra, a support, solidary with said fastener in a unique orientation relative to said fastener, a detector, removably secured to said support in a unique orientation relative to said support and adapted to measure one or more parameters representative of said patient spine vertebra angular orientation.

This object is also achieved with a set of sensors according to the invention.

This object is also achieved with a sensing method using a set of sensors according to the invention.

Preferred embodiments comprise one or more of the following features, which can be taken separately or together, either in partial combination or in full combination, in combination with any of previous objects of the invention.

Preferably, said fastener is specific to said specific patient spine vertebra. This way, the unique orientation of the fastener relative the specific vertebra can be more easily obtained.

Preferably, said fastener shape is complementary to said specific patient spine vertebra shape so that said specific patient spine vertebra can be nested in said fastener. This way, not only can the unique orientation of the fastener relative the specific vertebra be more easily obtained, but also this got unique orientation may be more robustly held over time.

Preferably, said fastener shape is complementary to a rear rib shape of said specific patient spine vertebra. The rear rib of the vertebra is easily attainable; therefore the fastener may be easily fastened on it. Besides, the vicinity of the rear rib of the vertebra is less cluttered; therefore the detector associated to the fastener may more easily perform the required measurement.

Preferably, said support is removable from said fastener. This way, fewer supports than fasteners are needed.

Preferably, said support extends said fastener, perpendicularly to spine axis. This way, the detector can more easily perform the required measurement when the fastener is fastened on the rear rib of the vertebra.

Preferably, said support is specific to said specific patient spine vertebra. The support can thereby be made integral with the fastener and no fixing or linking device between fastener and support is needed.

Preferably, said support general shape is generic for all spine vertebrae of all patients and said support orientation is specific to said specific patient spine vertebra. This way, the support structure is simpler and the associated cost is cheaper, whereas the required unique orientation of the support relative to the fastener can still be easily achieved.

Preferably, said support general shape is oriented with a known orientation relative to an upper or a lower average plate of said specific patient spine vertebra. Knowing orientation relative to one or to the other of the vertebra plates allows for determining more easily the angular orientation of the vertebra.

Preferably, said support general shape is a plate which is oriented parallel to an upper or a lower average plate of said specific patient spine vertebra. This makes a very simple and cheap support shape, whereas its required function, providing the required unique orientation, is still fulfilled.

Preferably, said detector is generic for all spine vertebrae of all patients. This is particularly interesting because the detector is the more complicated part of the sensor, since it contains the components able to perform the required measurements. So, it is particularly interesting to make this complicated part of the sensor generic, lowering thereby its cost.

Preferably, said detector can be clipped on said support. This is a quick and efficient way to fasten an object which is quite light and which still needs to be motionless relative to its support, in order to maintain easily the unique orientation of the detector relative to its support over time, at least during measurement step.

Preferably, said detector includes one or more gyroscopes, and/or one or more accelerometers, and/or one or more magnetometers, adapted to measure one or more parameters representative of said patient spine vertebra angular orientation. This way, the required measurements may be easily performed despite the cluttered space surrounding the patient spine. Such required measurements would be somewhat more difficult to get via signal emission outside the detector itself.

Preferably, said detector also includes a microprocessor to process measured parameters and/or a short range, preferably Bluetooth, emitter to send out said processed parameters. This way, the detector structure may be made simpler and the detector may be made smaller, since it will be located in a cluttered space surrounding the patient spine, whereas part of the components dedicated to signal processing will be deported farther from the cluttered vicinity of the patient spine.

Preferably, said detector performs real time measurement. This is interesting since the surgeon has a limited time when performing operative treatment while using such sensors.

Preferably, said fastener and said support orientation have been designed from a 3D image of said patient spine, which is preferably a 3D reconstruction of said patient spine from two 2D radiographic images of said patient spine. Therefore, the unique orientations of one sensor element with respect to another sensor element can be precisely estimated whereas the required information to do so can be got in a rather simple way. These two 2D radiographic images of said patient spine are advantageously a frontal x-ray image and a lateral x-ray image.

Preferably, said set of sensors comprises strictly fewer detectors than couples of fastener and support. Thereby some detectors may be mutualized. Besides, that is all the better, since the detectors containing the electronic components are the most expensive to build, whereas the fasteners and supports being only mechanical elements are easier and cheaper to build, at least before being customized to the specific corresponding vertebrae.

Preferably, said set of sensors comprises 2 detectors coupled to each other, having been preferably calibrated relatively to each other. This allows for more precise measurement, whereas the number of required detectors is kept to a minimum.

Preferably, said set of sensors comprises 6 couples of fastener and support. Only a third of detectors relative to the number of said couples is needed: this shows a high rate of mutualizing detectors.

Preferably, said sensing method comprises a step of positioning all couples of fastener and support on corresponding patient spine vertebrae, or a step of positioning all couples of fastener and support on corresponding patient spine vertebrae and/or on a sacral plate, a step of performing angular orientation measurements, comprising: a sub-step of positioning said detectors on some of said couples of fastener and support, a sub-step of performing an angular orientation measurement, a sub-step of repositioning said detectors on some others of said couples of fastener and support, a sub-step of performing another angular orientation measurement, the two last sub-steps being performed once or more times. This way, if the detectors have to be moved from one location to the other, the fasteners, as far as they are concerned, which are the trickiest to set up, do not need to be moved during the whole measurement phase.

Preferably, said couples of fastener and support are positioned on patient spine vertebrae which comprise cervical vertebrae and/or thoracic vertebrae and/or lumbar vertebrae, and/or on patient sacral plate, in order to measure curvature of kyphosis and/or lordosis. The angular orientations of vertebrae, when estimating curvature of kyphosis and/or lordosis, are critical.

Preferably, said couples of fastener and support are positioned on patient spine vertebrae which comprise thoracic vertebrae T1, T4 and T12, and lumbar vertebrae L1 and L5, as well as on sacral plate S1. These locations are the more interesting in order to get, with a limited number of fasteners and of measurement steps, the most accurate angular orientation measurements leading to the most accurate estimation of kyphosis and/or of lordosis.

Further features and advantages of the invention will appear from the following description of embodiments of the invention, given as non-limiting examples, with reference to the accompanying drawings listed hereunder.

DETAILED DESCRIPTION OF THE INVENTION

Figure 1:
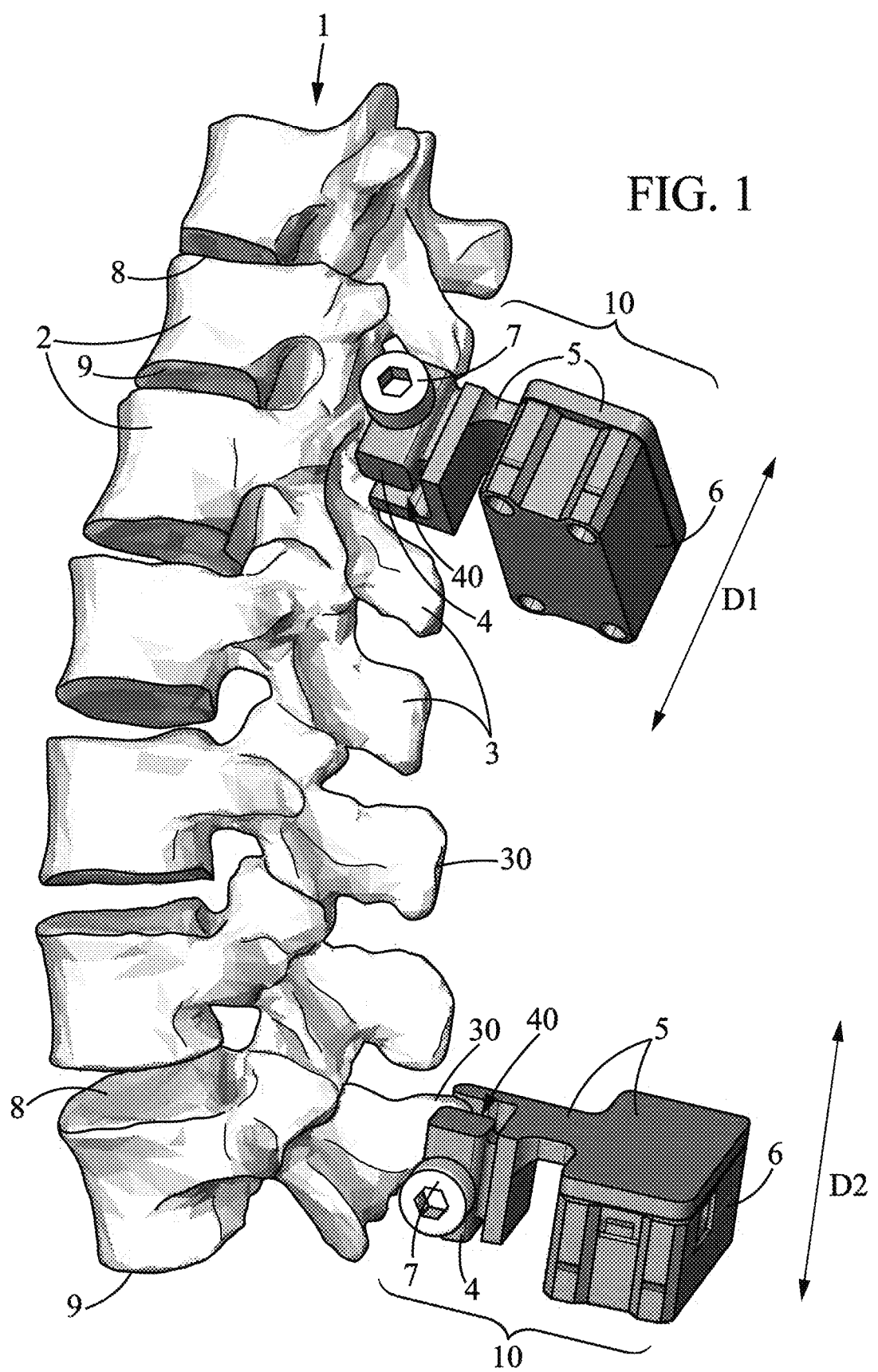
FIG. 1 shows a view in perspective of an example of sensors fastened on a patient spine, such sensors being structured according to an embodiment of the invention.

FIG. 1 shows a view in perspective of an example of sensors fastened on a patient spine, such sensors being structured according to an embodiment of the invention.

A portion of a vertebral spine 1 comprises vertebrae 2. These vertebrae 2 may comprise thoracic and/or lumbar vertebrae. These vertebrae 2 may even include one or more cervical vertebrae. Each vertebra 2 comprises an upper plate 8, relatively plan or at least presenting an average plan, and a lower plate 9, relatively plan or at least presenting an average plan. Each vertebra 2 also comprises a rear rib 3 which is much more easily accessible during operative treatment than would be its upper plate 8 or its lower plate 9. The rear rib 3 presents a protuberance 30. This protuberance 30 is to be nested within a corresponding internal recess 40 of the fastener 4 of the corresponding sensor 10.

On the spine 1 are implemented two sensors 10 which are disposed to be able to measure the patient spine vertebra angular orientation. Each sensor 10 includes a fastener 4, a support 5 and a detector 6. Each sensor 10 is secured to the spine 1 via a screw 7 or via a pin. More precisely, each fastener 4 is secured to the rear rib 3 via the screw 7 or via the pin. The fastener 4 includes an internal recess 40 adapted to receive the protuberance 30 of the rear rib 3 of the corresponding vertebra 2.

The sensing method uses a set of sensors 10. In this sensing method, the couples of fastener 4 and support 5 are positioned on vertebrae 2 which comprise thoracic vertebrae and/or lumbar vertebrae, and/or on the sacral plate of the patient, in order to measure curvature of kyphosis and/or curvature of lordosis. More precisely, the couples of fastener 4 and support 5 are positioned on vertebrae 2 which comprise thoracic vertebrae T1, T4 and T12, and lumbar vertebrae L1 and L5, as well as on sacral plate S1. This method includes successively a step of positioning the couples of fastener 4 and support 5 and a step of performing angular orientation measurements. First, there is a step of positioning all couples of fastener 4 and support 5 on corresponding vertebrae 2, or a step of positioning all couples of fastener 4 and support 5 on corresponding vertebrae 2 and/or on a sacral plate.

Then, afterwards, during the whole step of performing angular orientation measurements, these couples of fastener 4 and support 5 will remain fixed and will no more be moved before the end of this step of performing angular orientation measurements which includes the following sub-steps. First, there is a sub-step of positioning the detectors 6 on some couples of fastener 4 and support 5. Second, there is a sub-step of performing an angular orientation measurement, concerning the portion of spine located between both fasteners 4. Third, there is a sub-step of repositioning said detectors 6 on some others couples of fastener 4 and support 5. Fourth, there is a sub-step of performing another angular orientation measurement, concerning the other portion of spine located between both other fasteners 4. Third and fourth sub-steps can be performed once or more times, depending on how many measurements are to be performed, that is on how many couples of fastener and support have been implemented on how many corresponding portions of spine.

The fastener 4 is adapted to be fastened on a specific patient spine vertebra 2 in a unique orientation relative to this specific vertebra 2. Each fastener 4 is specific to the corresponding vertebra 2. Each fastener 4 shape is complementary to the specific vertebra 2 shape so that this specific vertebra 2 can be nested in this fastener 4. Each fastener 4 shape is complementary to a rear rib 3 shape of its corresponding specific vertebra 2.

The support 5 is solidary with the fastener 4 in a unique orientation relative to this fastener 4. Each support 5 is removable from its fastener 4. Each support 5 extends its fastener 4, advantageously perpendicularly to the axis of the spine 1. Each support 5 general shape is generic for all vertebrae 2 of all patients and the orientation of this support 5 is specific to the specific corresponding vertebra 2. Each support 5 general shape is oriented with a known orientation relative to an upper 8 or a lower 9 average plate of this specific corresponding vertebra 2. Each support 5 general shape is a plate which is oriented parallel to an upper 8 or a lower 9 average plate of this specific corresponding vertebra 2.

The detector 6 is removably secured to the support 5 in a unique orientation relative to this support 5 and is adapted to measure one or more parameters representative of the angular orientation of the vertebra 2. The detector 6 of the upper sensor 10 is oriented parallel to a first direction D1. The detector 6 of the lower sensor 10 is oriented parallel to a second direction D2. Both sensors 10 have been calibrated relative to each other in a preliminary step before being implemented on the spine 1. Determining the relative angular orientation of those directions D1 and D2 in the three dimensional space allows for determining the orientation, more precisely the curvature, of the portion of spine 1 located between the two vertebrae 2 on which the two sensors 10, more precisely their fasteners 4, are implemented. This determination of the relative angular orientation of those directions D1 and D2 in the three dimensional space is done via the representative parameters measured by the two sensors 10, when moving from their respective calibration positions to their respective implementations in situ on their vertebrae 2 of the spine 1.

Each detector 6 is generic for all vertebrae 2 of all patients. Each detector 6 can be clipped on its support 5 to make the required measurement, and then can be removed by being unclipped, and afterwards can be clipped again, but this time on another support 5, to make another required measurement. Each detector 6 includes one or more gyroscopes measuring the rotations undergone by the detector 6, and/or one or more accelerometers measuring the accelerations undergone by the detector 6, the group of all these parameters being representative of the angular orientation of the vertebra 2. Each detector 6 also includes a microprocessor to process measured parameters and/or a short range, preferably Bluetooth, emitter to send out said processed parameters. Each detector 6 performs real time measurement.

Once all required measurements have been performed during operative treatment, all sensors 10, including all fasteners 4, supports 5, detectors 6 and screws 7, are removed before end of this operative treatment.

Figure 2:
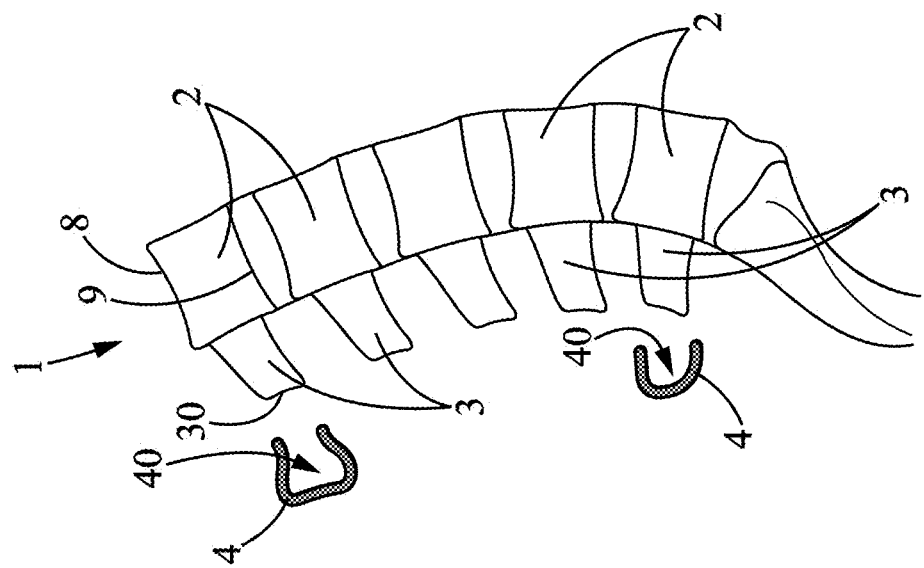
FIG. 2 shows a lateral view of an example of shapes of sensor fasteners to be fastened on a patient spine, such sensor fasteners belonging to sensors being structured according to an embodiment of the invention.

FIG. 2 shows a lateral view of an example of shapes of sensor fasteners to be fastened on a patient spine, such sensor fasteners belonging to sensors being structured according to an embodiment of the invention.

Here, for sake of clarity reasons, only the shapes of the fasteners 4 of the sensors have been represented on FIG. 2, neither their supports nor their detectors being represented. The shape of the internal recess 40 of the fastener 4 is clearly visible. Within this internal recess 40 will be nested the protuberance 30 of the rear rib 3 to which this fastener 4 is dedicated. This internal recess 40 of the fastener 4 and this protuberance 30 of the rear rib 3 are complementary to each other, and even preferably present exactly complementary shapes, so that the protuberance 30 of the rear rib 3 is nested, and preferably is perfectly nested, within the internal recess 40 of the fastener 4. On the FIG. 2, the internal recesses 40 of the fasteners 4 are presented face to face with their corresponding protuberances 30 of the rear ribs 3, but at some distance from each other, not yet nested within each other, and indeed just before being nested within each other.

The position and orientation of all parts of the vertebrae 2 of the spine 1 can be known via the radiographic images and via a three dimensional reconstruction associated to these radiographic images. The position and orientation of all elements of the sensors 10 can be known via the known structure of these sensors 10.

The relative orientation of the internal recess 40 of the fastener 4 on the one side and of the protuberance 30 of the rear rib 3 on the other side is fixed because of the nesting of the protuberance 30 of the rear rib 3 within the internal recess 40 of the fastener 4, and is known.

Since the relative orientation of all parts of a vertebra 2 relative to one another is fixed, because the vertebra is integral, and can be known, and since the relative orientation of all elements of the corresponding sensor 10 to one another is fixed, because of the solidary attachment of these elements to one another, and can be known, the fixed and known relative orientation of the internal recess 40 of the fastener 4 and of the protuberance 30 of the rear rib 3 leads to a fixed and determinable relative orientation between the measuring detector 6 of the sensor 10 on the one side and the upper 8 (or lower 9) plate de the corresponding vertebra 2 on the other side.

Figure 3:
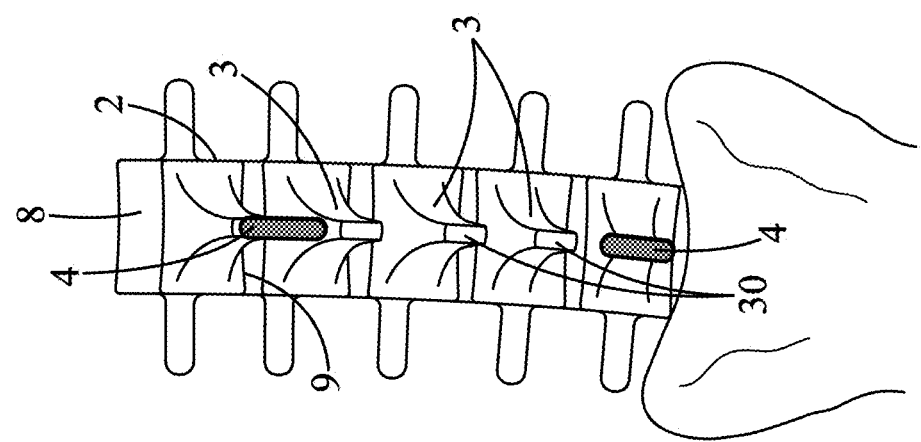
FIG. 3 shows a front view of an example of shapes of sensor fasteners to be fastened on a patient spine, such sensor fasteners belonging to sensors being structured according to an embodiment of the invention, this front view corresponding to the lateral view of FIG. 2.

FIG. 3 shows a front view of an example of shapes of sensor fasteners to be fastened on a patient spine, such sensor fasteners belonging to sensors being structured according to an embodiment of the invention, this front view corresponding to the lateral view of FIG. 2.

The internal recesses 40 of the fasteners 4 are rather flat elements in a plan orthogonal to the plan of FIG. 3. This makes the fastener 4 a simpler and compacter element.

However, the internal recess 40 of the fastener 4 could encompass more volume of the protuberance 30 of the rear rib 3. The corresponding fastener 4 would be more cumbersome but would allow for a better and more robust holding of the relative position between fastener 4 and corresponding vertebra 2.

The invention has been described with reference to preferred embodiments. However, many variations are possible within the scope of the invention.

The invention claimed is:

1. Sensor measuring patient spine (1) vertebra (2) angular orientation, comprising:
    a fastener (4), adapted to be fastened on a specific patient spine (1) vertebra (2) in a unique orientation relative to said specific vertebra (2),
    a support (5), solidary with said fastener (4) in a unique orientation relative to said fastener (4),
    a detector (6), removably secured to said support (5) in a unique orientation relative to said support (5) and adapted to measure one or more parameters representative of said patient spine (1) vertebra (2) angular orientation.

2. Sensor according to claim 1, wherein said fastener (4) is specific to said specific patient spine (1) vertebra (2).

3. Sensor according to claim 2, wherein said fastener (4) shape is complementary to said specific patient spine (1) vertebra (2) shape so that said specific patient spine (1) vertebra (2) can be nested in said fastener (4).

4. Sensor according to claim 3, wherein said fastener (4) shape is complementary to a rear rib (3) shape of said specific patient spine (1) vertebra (2).

5. Sensor according to claim 1, wherein said support (5) is removable from said fastener (4).

6. Sensor according to claim 1, wherein said support (5) extends said fastener (4), perpendicularly to spine (1) axis.

7. Sensor according to claim 1, wherein said support (5) is specific to said specific patient spine (1) vertebra (2).

8. Sensor according to claim 7, wherein said support (5) general shape is generic for all spine (1) vertebrae (2) of all patients and said support (5) orientation is specific to said specific patient spine (1) vertebra (2).

9. Sensor according to claim 1, wherein said support (5) general shape is oriented with a known orientation relative to an upper (8) or a lower (9) average plate of said specific patient spine (1) vertebra (2).

10. Sensor according to claim 9, wherein said support (5) general shape is a plate which is oriented parallel to an upper (8) or a lower (9) average plate of said specific patient spine (1) vertebra (2).

11. Sensor according to claim 1, wherein said detector (6) is generic for all spine (1) vertebrae (2) of all patients.

12. Sensor according to claim 1, wherein said detector (6) can be clipped on said support (5).

13. Sensor according to claim 1, wherein said detector (6) includes one or more gyroscopes, and/or one or more accelerometers, and/or one or more magnetometers, adapted to measure one or more parameters representative of said patient spine (1) vertebra (2) angular orientation.

14. Sensor according to claim 13, wherein said detector (6) also includes a microprocessor to process measured parameters and/or a short range emitter to send out said processed parameters.

15. Sensor according to claim 1, wherein said detector (6) performs real time measurement.

16. Sensor according to claim 1, wherein said fastener (4) and said support (5) orientation have been designed from a 3D image of said patient spine (1).

17. Set of sensors (10) according to claim 1, wherein said set of sensors (10) comprises strictly fewer detectors (6) than couples of fastener (4) and support (5).

18. Set of sensors (10) according to claim 17, wherein said set of sensors (10) comprises 2 detectors (6) coupled to each other.

19. Set of sensors (10) according to claim 18, wherein said set of sensors (10) comprises 6 couples of fastener (4) and support (5).

20. Sensing method using a set of sensors (10) according to claim 17, wherein it comprises:
    a step of positioning all couples of fastener (4) and support (5) on corresponding patient spine (1) vertebrae (2), or a step of positioning all couples of fastener (4) and support (5) on corresponding patient spine (1) vertebrae (2) and/or on a sacral plate,
    a step of performing angular orientation measurements, comprising:
        a sub-step of positioning said detectors (6) on some of said couples of fastener (4) and support (5),
        a sub-step of performing an angular orientation measurement,
        a sub-step of repositioning said detectors (6) on some others of said couples of fastener (4) and support (5),
        a sub-step of performing another angular orientation measurement,
        the two last sub-steps being performed once or more times.

21. Sensing method according to claim 20, wherein said couples of fastener (4) and support (5) are positioned on patient spine (1) vertebrae (2) which comprise thoracic vertebrae and/or lumbar vertebrae, and/or on patient sacral plate, in order to measure curvature of kyphosis and/or lordosis.

22. Sensing method according to claim 21, wherein said couples of fastener (4) and support (5) are positioned on patient spine (1) vertebrae (2) which comprise thoracic vertebrae T1, T4 and T12, and lumbar vertebrae L1 and L5, as well as on sacral plate S1.

\* \* \* \* \*